United States Patent
Bailey et al.

(10) Patent No.: US 7,439,240 B2
(45) Date of Patent: Oct. 21, 2008

(54) PURINE-OR PYRROLOL[2,3-D]PYRIMIDINE-2-CARBONITILES FOR TREATING DISEASES ASSOCIATED WITH CYSTEINE PROTEASE ACTIVITY

(75) Inventors: Andrew Bailey, Loughborough (GB); Garry Pairaudeau, Loughborough (GB); Anil Patel, Loughborough (GB); Stephen Thom, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 278 days.

(21) Appl. No.: 10/518,815

(22) PCT Filed: Jun. 23, 2003

(86) PCT No.: PCT/SE03/01079

§ 371 (c)(1),
(2), (4) Date: Dec. 20, 2004

(87) PCT Pub. No.: WO04/000843

PCT Pub. Date: Dec. 31, 2003

(65) Prior Publication Data

US 2005/0203107 A1   Sep. 15, 2005

(30) Foreign Application Priority Data

Jun. 24, 2002 (SE) .................... 0201980

(51) Int. Cl.
| C07D 473/30 | (2006.01) |
| C07D 473/34 | (2006.01) |
| A61K 31/52 | (2006.01) |
| A61K 31/522 | (2006.01) |
| A61P 25/04 | (2006.01) |
| C07D 487/04 | (2006.01) |
| C07D 473/40 | (2006.01) |
| A61K 31/519 | (2006.01) |

(52) U.S. Cl. ............ 514/234.2; 514/263.1; 514/263.2; 514/263.22; 514/263.4; 544/118; 544/265; 544/277; 544/117; 544/328; 544/329; 544/280; 544/299; 544/262

(58) Field of Classification Search .............. 514/234.2, 514/263.1, 263.2, 263.22, 263.4; 544/118, 544/265, 277

See application file for complete search history.

(56) References Cited

U.S. PATENT DOCUMENTS

| 6,921,753 B2 * | 7/2005 | Mantell et al. ................ 514/46 |
| 2002/0132819 A1 | 9/2002 | Metcalf et al. |
| 2006/0142575 A1 * | 6/2006 | Altmann et al. ............. 544/277 |

FOREIGN PATENT DOCUMENTS

| EP | 1724264 A1 | 11/2006 |
| WO | WO 0055125 A2 | 9/2000 |
| WO | WO 0232879 A1 | 4/2002 |
| WO | 03020278 A1 | 3/2003 |
| WO | WO 03020721 A1 | 3/2003 |
| WO | 2004069256 A1 | 8/2004 |
| WO | 2004076455 A1 | 9/2004 |
| WO | 2005085210 A1 | 9/2005 |
| WO | 2006040300 A1 | 4/2006 |

OTHER PUBLICATIONS

International Search Report.
International-Type Search Report.
STN International, CAPLUS accession No. 1991:484886, document No. 115:84886, NAIR, Vasu et al., "Inhibition of mammalian . . . -dideoxyadenosines", & Biochemica et Biophysica Acta (1991), 1078(1), 121-3.
Database WPI, Week 200136, Derwent Publication Ltd., London, GB; AN 2001-337719 & JP 2001 011037 A (Kissei Yakuhin Kogyo KK), Jan. 16, 2001 Abstract.

* cited by examiner

*Primary Examiner*—Mark L Berch
(74) *Attorney, Agent, or Firm*—Jianzhong Shen

(57) ABSTRACT

The present invention therefore provides a compound of formula (I) and compositions for treating diseases associated with cysteine protease activity. The compounds are reversible inhibitors of cysteine proteases S, K, F, L and B. Of particular interest are diseases associated with Cathepsin S. In addition this invention also discloses processes for the preparation of such inhibitors.

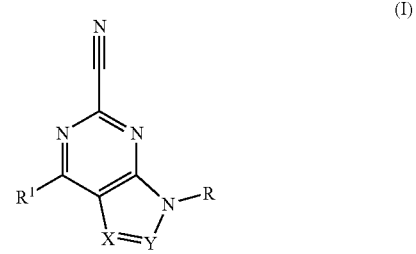

(I)

14 Claims, No Drawings

PURINE-OR PYRROLOL[2,3-D]PYRIMIDINE-2-CARBONITILES FOR TREATING DISEASES ASSOCIATED WITH CYSTEINE PROTEASE ACTIVITY

The present invention relates to compounds and compositions for treating diseases associated with cysteine protease activity. The compounds are reversible inhibitors of cysteine proteases S, K, F, L and B. Of particular interest are diseases associated with Cathepsin S. In addition this invention also discloses processes for the preparation of such inhibitors.

BACKGROUND OF THE INVENTION

Cathepsin S is a member of the papain superfamily of cysteine proteases which also encompasses Cathepsins B, H, L, O and K. Cathepsin S plays a key role in the processing of invariant chain in MHC class II complexes allowing the complex to associate with antigenic peptides. MHC class II complexes are then transported to the surface of the cell for presentation to effector cells such as T cells. The process of antigen presentation is a fundamental step in initiation of the immune response. In this respect inhibitors of cathepsin S could be useful agents in the treatment of inflammation and immune disorders such as, but not limited to, asthma, rheumatoid arthritis, multiple sclerosis and Crohn's disease. Cathepsin S has also been implicated in a variety of other diseases involving extracellular proteolysis such as the development of emphysema in COPD through degradation of elastin and in Alzheimers disease.

Other Cathepsins notably K and L have been shown to degrade bone collagen and other bone matrix proteins. Inhibitors of these cysteine proteases would be expected to be useful in the treatment of diseases involving bone resorption such as osteoporosis.

The present invention therefore provides a compound of formula (I)

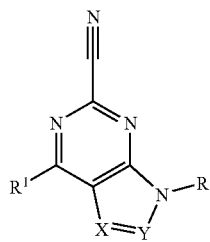

(I)

in which:

X is N, NH, :CH or $CH_2$;
Y is N, :CH, CO, $CH_2$ or $:CNR^2R^3$, where $R^2$ and $R^3$ are independently hydrogen, $C_{1-6}$ alkyl or $C_{3-6}$ cycloalkyl;
R is aryl or heteroaryl optionally substituted by halogen, amino, hydroxy, cyano, nitro, trifluoromethyl, carboxy, $CONR^5R^6$, $SO_2NR^5R^6$, $SO_2R^4$, $NHSO_2R^4$, $NHCOR^4$, ethylenedioxy, methylenedioxy, $C_{1-6}$ alkyl, $C_{1-6}$ alkoxy, $SR^4$ or $NR^5R^6$ where R4 is hydrogen, $C_{1-6}$ alkyl or $C_{3-6}$ cycloalkyl, $R^5$ and $R^6$ are independently hydrogen, $C_{1-6}$ alkyl or together with the nitrogen atom to which they are attached form a 5- or 6-membered saturated ring optionally containing a further O, S or $NR^4$ group;
or R is hydrogen, $C_{1-6}$ alkyl or $C_{3-6}$ cycloalkyl both of which can optionally contain one or more O, S or $NR^4$ groups,
$R^1$ is a group $Y(CH_2)pR^7$ where p is 0, 1 or 2 and Y is O or $NR^8$ where $R^8$ is hydrogen, $C_{1-6}$ alkyl or $C_{3-6}$ cycloalkyl;
and $R^7$ is a 5- or 6-membered saturated ring containing one or more O, S or N atoms, aryl or a heteroaryl group containing one to four heteroatoms selected from O, S or N, the saturated ring, aryl and heteroaryl groups all being optionally substituted by halogen, amino, hydroxy, cyano, nitro, trifluoromethyl, carboxy, $CONR^5R^6$, $SO_2NR^5R^6$, $SO_2R^4$, $NHSO_2R^4$, $NHCOR^4$, $C_{1-6}$ alkyl, $C_{1-6}$ alkoxy, $SR^4$ or $NR^5R^6$ where R4 is hydrogen, $C_{1-6}$ alkyl or $C_{3-6}$ cycloalkyl, $R^5$ and $R^6$ are independently hydrogen, $C_{1-6}$ alkyl or together with the nitrogen atom to which they are attached form a 5- or 6-membered saturated ring optionally containing a further O, S or $NR^4$ group;
or $R^1$ is a group $NR^9R^{10}$ where $R^9$ and $R^{10}$ are independently hydrogen or $C_{1-6}$ alkyl optionally containing one or more O, S or $NR^4$ groups, or $R^9$ and $R^{10}$ together with the nitrogen atom to which they are attached form a 5 or 6-membered saturated ring optionally containing a further O, S or N atom and optionally substituted by $NR^9R^{10}$, $CO_2C_{1-6}$ alkyl, $CONR^{11}R^{12}$ where $R^{11}$ and $R^{12}$ are independently hydrogen or $C_{1-6}$ alkyl, aryl or heteroaryl group optionally substituted by halogen, amino, hydroxy, cyano, nitro, trifluoromethyl, carboxy, $CONR^5R^6$, $SO_2NR^5R^6$, $SO_2R^4$, $NHSO_2R^4$, $NHCOR^4$, $C_{1-6}$ alkyl, $C_{1-6}$ alkoxy, $SR^4$ or $NR^5R^6$ where R4 is hydrogen, $C_{1-6}$ alkyl or $C_{3-6}$ cycloalkyl, $R^5$ and $R^6$ are independently hydrogen, $C_{1-6}$ alkyl or together with the nitrogen atom to which they are attached form a 5- or 6-membered saturated ring optionally containing a further O, S or $NR^4$ group;
and pharmaceutically acceptable salts or solvates thereof.

In the context of the present specification, unless otherwise indicated, an alkyl or alkenyl group or an alkyl or alkenyl moiety in a substituent group may be linear or branched. Aryl groups include phenyl and naphthyl. Heteroaryl groups include 5- or 6-membered, 5,6- or 6,6-fused aromatic rings containing one or more heteroatoms selected from N, S, O. Examples include pyridine, pyrimidine, pyrazine, pyridazine, thiazole, oxazole, pyrazole, imidazole, furan and thiophene, quinoline, isoquinoline, benzimidazole, benzofuran, benzothiophene, indole.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Preferably X is N and Y is :CH, X and Y are:CH or X and Y are $CH_2$

Preferably R is $C_{1-4}$alkyl, or phenyl substituted by halogen, in particular chloro, $SO_2Me$, $C_{1-6}$alkoxy, in particular methoxy, $C_{1-4}$alkyl, in particular methyl or propyl.

Preferably $R^1$ is a group $Y(CH_2)pR^7$ where p is 0 and Y is $NR^8$ where $R^8$ is hydrogen and $R^7$ is substituted phenyl. Preferably $R^7$ is phenyl substituted by halogen, especially chloro; or $R^1$ is $NR^9R^{10}$ where $R^9$ and $R^{10}$ are hydrogen or $C_{1-3}$ alkyl or together with the nitrogen atom to which they are attached form a 5 or 6-membered saturated ring optionally containing a O, S or $NR^4$.

Preferred compounds of the invention include:
1-[9-(4-Chlorophenyl)-2-cyano-9H-purin-6-yl]-L-prolinamide,
9-(4-Chlorophenyl)-6-(4-pyrrolidin-1-ylpiperidin-1-yl)-9H-purine-2-carbonitrile,
9-(4-Chlorophenyl)-6-[(3-pyrrolidin-1-ylpropyl)amino]-9H-purine-2-carbonitrile,
6-(4-Aminopiperidin-1-yl)-9-(4-chlorophenyl)-9H-purine-2-carbonitrile,
6-[(2-Aminoethyl)amino]-9-(4-chlorophenyl)-9H-purine-2-carbonitrile,
9-(4-Chlorophenyl)-6-(dimethylamino)-9H-purine-2-carbonitrile,
9-(4-Methylphenyl)-6-pyrrolidin-1-yl-9H-purine-2-carbonitrile, 9-(4-Methoxyphenyl)-6-pyrrolidin-1-yl-9H-purine-2-carbonitrile,
9-(4-chlorophenyl)-6-pyrrolidin-1-yl-9H-purine-2-carbonitrile,
9-(4-Chlorophenyl)-6-(ethylamino)-9H-purine-2-carbonitrile,
tert-Butyl 4-[9-(4-chlorophenyl)-2-cyano-9H-purine-6-yl]piperazine-1-carboxylate,
9-(4-Chlorophenyl)-6-piperazin-1-yl-9H-purine-2-carbonitrile,
9-(2-Chlorophenyl)-6-morpholin-4-yl-9H-purine-2-carbonitrile
9-(3,4-Difluorophenyl)-6-morpholin-4-yl-9H-purine-2-carbonitrile,
9-(4-Isopropylphenyl)-6-morpholin-4-yl-9H-purine-2-carbonitrile,
9-(4-Methoxyphenyl)-6-morpholin-4-yl-9H-purine-2-carbonitrile,
9-(3-Chlorophenyl)-6-morpholin-4-yl-9H-purine-2-carbonitrile,
9-[4-(Methylsulfonyl)phenyl]-6-morpholin-4-yl-9H-purine-2-carbonitrile,
6-[(4-Chlorophenyl)amino]-9-ethyl-9H-purine-2-carbonitrile,
9-(4-Chlorophenyl)-6-morpholin-4-yl-9H-purine-2-carbonitrile,
8-Amino-6-[(4-chlorophenyl)amino]-9-ethyl-9H-purine-2-carbonitrile,
8-Amino-9-(4-chlorophenyl)-6-morpholin-4-yl-9H-purine-2-carbonitrile,
9-(4-Chlorophenyl)-6-morpholin-4-yl-8-oxo-8,9-dihydro-7H-purine-2-carbonitrile,
9-(4-Chlorophenyl)-8-(dimethylamino)-6-morpholin-4-yl-9H-purine-2-carbonitrile,
7-(4-Chlorophenyl)-4-morpholin-4-yl-7H-pyrrolo[2,3-d]pyrimidine-2-carbonitrile,
7-(4-Chlorophenyl)-4-(ethylamino)-7H-pyrrolo[2,3-d]pyrimidine-2-carbonitrile,
4-[(4-Chlorophenyl)amino]-7-ethyl-7H-pyrrolo[2,3-d]pyrimidine-2-carbonitrile,
1-[7-(4-Chlorophenyl)-2-cyano-6,7-dihydro-5H-pyrrolo[2,3-d]pyrimidin-4-yl]-L-prolinamide,
1-[2-Cyano-7-(4-methoxyphenyl)-6,7-dihydro-5H-pyrrolo[2,3-d]pyrimidin-4-yl]-L-prolinamide,
7-(4-Methoxyphenyl)-4-pyrrolidin-1-yl-6,7-dihydro-5H-pyrrolo[2,3-d]pyrimidine-2-carbonitrile,
7-(4-Methoxyphenyl)-4-morpholin-4-yl-6,7-dihydro-5H-pyrrolo[2,3-d]pyrimidine-2-carbonitrile,
1-(4-Methylphenyl)-4-morpholin-4-yl-1H-pyrazolo[3,4-d]pyrimidine-6-carbonitrile, and pharmaceutically acceptable salts thereof.

The present invention further provides a process for the preparation of a compound of formula (I) which comprises
(i) reaction of a compound of general formula (II)

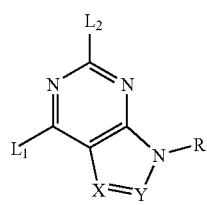
(II)

wherein L1 and L2 represent a leaving group (e.g. halide, sulphide, sulfoxide or sulphone group), preferably the sulphide is oxidised to a sulphoxide or sulphone group before displacement. An oxidising agent such as a peracid may be used, for example metachloroperbenzoic acid in dichloromethane at room temperature.

L1 may be displaced by $R^1$ where $R^1$ is defined in formula (I) and L2 may be displaced by cyanide, preferably using a salt (e.g. lithium, sodium or potassium cyanide). The sequence of displacement of L1, L2 may be varied.

Compounds of formula (II) where X=N and Y=:CH or :CNR$^2$R$^3$ may be prepared from compounds of formula (III) by ring cyclisations using, for example diethoxymethyl acetate, FMOC-NCS or R$^3$R$^2$NCSCl. Compounds of formula (II) where X=NH and Y=CO can also be prepared from compounds of formula (III) by reaction with phosgene or phosgene equivalent. The sequence of steps may also be varied, for example compounds of formula (III) may first have L1 and/or L2 displaced before the cyclisation step.

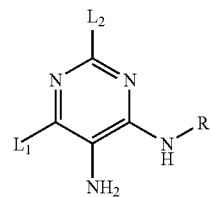
(III)

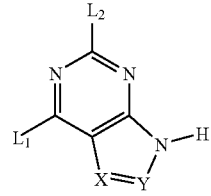
(IV)

Compounds of formula (II) may also be prepared from compound of formula (IV) by reaction with a group R—Z, where R is defined in formula (I) and Z is a leaving group (e.g. halide, activated alcohol).

Compounds of formula (II) where X and Y=:CH may also be prepared from compounds of formula (V) and compounds of formula (II) where X and Y=CH$_2$ may also be formed from compounds of formula (VI).

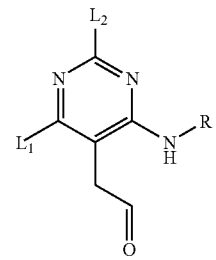
(V)

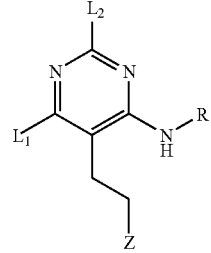
(VI)

According to a further feature of the invention there is provided a compound of the formula (I), or a pharmaceutically acceptable salt thereof, for use as a therapeutic agent.

According to a further feature of the present invention there is provided a method for producing inhibition of a cysteine protease in a warm blooded animal, such as man, in need of such treatment, which comprises administering to said animal an effective amount of a compound of the present invention, or a pharmaceutically acceptable salt thereof.

The invention also provides a compound of the formula (I), or a pharmaceutically acceptable salt thereof, for use as a medicament; and the use of a compound of the formula (I) of the present invention, or a pharmaceutically acceptable salt thereof, in the manufacture of a medicament for use in the inhibition of a cysteine protease in a warm blooded animal, such as man. In particular the compounds of the invention are useful in the treatment of inflammation and immune disorders such as, but not limited to, asthma, rheumatoid arthritis, COPD, multiple sclerosis, Crohn's disease, Alzheimers and pain, such as neuropathic pain. Preferably the compounds of the invention are used to treat pain, especially neuropathic pain.

In particular the invention provides the use of a compound of the formula (I) of the present invention, or a pharmaceutically acceptable salt thereof, in the manufacture of a medicament for use in the inhibition of Cathepsin S in a warm blooded animal, such as man. In order to use a compound of the formula (I) or a pharmaceutically acceptable salt thereof for the therapeutic treatment of mammals including humans, in particular in the inhibition of a cysteine protease, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt thereof and a pharmaceutically acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 100 mg and 1 g of the compound of this invention.

In another aspect a pharmaceutical composition of the invention is one suitable for intravenous, subcutaneous or intramuscular injection.

Each patient may receive, for example, an intravenous, subcutaneous or intramuscular dose of 1 mgkg$^{-1}$ to 100 mgkg$^{-1}$ of the compound, preferably in the range of 5 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I), or a pharmaceutically-acceptable salt thereof (hereafter compound X), for therapeutic or prophylactic use in humans:

| (a) | |
|---|---|
| Tablet I | mg/tablet |
| Compound X. | 100 |
| Lactose Ph.Eur. | 179 |
| Croscarmellose sodium | 12.0 |
| Polyvinylpyrrolidone | 6 |
| Magnesium stearate | 3.0 |

| (b) | |
|---|---|
| Tablet II | mg/tablet |
| Compound X | 50 |
| Lactose Ph.Eur. | 229 |
| Croscarmellose sodium | 12.0 |
| Polyvinylpyrrolidone | 6 |
| Magnesium stearate | 3.0 |

| (c) | |
|---|---|
| Tablet III | mg/tablet |
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

| (d) | |
|---|---|
| Capsule | mg/capsule |
| Compound X | 10 |
| Lactose Ph.Eur. | 389 |
| Croscarmellose sodium | 100 |
| Magnesium stearate | 1. |

| (e) | |
|---|---|
| Injection I | (50 mg/ml) |
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β cyclodextrin may be used to aid formulation.

Note

The above formulations may be obtained by conventional procedures well known in the pharmaceutical art. The tablets (a)-(c) may be enteric coated by conventional means, for example to provide a coating of cellulose acetate phthalate.

The following examples illustrate the invention.

EXAMPLE 1

1-[9-(4-Chlorophenyl)-2-cyano-9H-purin-6-yl]-L-prolinamide (i) 6-Chloro-N-4-(4-chlorophenyl)-2-(propylthio)pyrimidine4,5-diamine A mixture of 4-chloroaniline (5.33g), N,N-diisopropylethylamine (7.3 ml) and 5-amino-4,6-dichloro-2-propylthiopyrimidine (10 g) was heated at 100° C. for 48 h. The mixture was partitioned between ethyl acetate and water, the organics dried (MgSO4), and evaporated under reduced pressure. The residue was purified by chromatography on silica eluting with 50% ethyl acetate in isohexane. Yield 4.6 g MS: APCI(+ve) 329(M+1)

(ii) 6-Chloro-9-(4-chlorophenyl)-2-(propylthio)-9H-purine

A solution of the product from step (i) (4.6 g) in diethoxymethylacetate (25 ml) was heated at 80° C. for 8 h. The mixture was added dropwise to a vigorously stirred mixture of water and isohexane (400 ml, 1:1), and the solid filtered. The solid was purified by chromatography on silica eluting with 25% ethyl acetate in isohexane. Yield 2.8 g MS: APCI(+ve) 339(M+1)

(iii) 6-Chloro-9-(4-chlorophenyl)-2-(propylsulfonyl)-9H-purine

A mixture of the product from step (ii) (2.8 g) and 3-chloroperoxybenzoic acid (3.6 g, Aldrich 77% max.) in dichloroethane (40 ml) was stirred at room temperature for 2 h, washed with aqueous sodium metabisulphite solution, water, aqueous sodium hydrogencarbonate solution, water, dried (MgSO4) and evaporated under reduced pressure. Yield 2.5 g MS: APCI(+ve) 371 (M+1)

(iv) 1-[9-(4-Chlorophenyl)-2-cyano-9H-purin-6-yl]-L-prolinamide

A solution of the product from step (iii) (0.2 g), L-prolinamide (0.062 g) and N,N-diisopropylethylamine (0.19 ml) in tetrahydrofuran (10 ml) was stirred at room temperature for 24 h. The solvent was removed, the residue dissolved in N,N-dimethylformamide (10 ml) and sodium cyanide (0.05 g) added and heated at 90° C. for 10 h. The mixture was partitioned between ethyl acetate and water, the organics dried (MgSO4) and evaporated under reduced pressure. The residue was purified by RPHPLC. Yield 0.062 g MS: APCI(+ve) 368(M+1) 1H NMR: (DMSO-d6) δ 8.67 (1H, s), 7.87-7.65(4H, 2×d), 6.95(2H, m), 4.08(2H, m), 2.97 (1H, m), 2.33-1.96(4H, m).

EXAMPLES 2-12

Examples 2-12 were prepared according to the general method of example 1 using the appropriate amines.

EXAMPLE 2

9-4-Chlorophenyl)-6-(4-pyrrolidin-1-ylpiperidin-1-yl)-9H-purine-2-carbonitrile

MS: APCI(+ve) 408(M+1) 1H NMR: (DMSO-d6) δ 8.79-8.77(1H, s), 7.87-7.70(4H, 2×d), 2.52-2.49(8H, m), 2.38-2.32(1H, m), 2.01-1.43(8H, m)

EXAMPLE 3

9-(4-Chlorophenyl)-6-[(3-pyrrolidin-1-ylpropyl)amino]-9H-purine-2-carbonitrile, trifluoroacetate salt MS: APCI(+ve) 382(M+1) 1H NMR: (DMSO-d6) δ 9.46 (1H, bs), 8.85-8.58(2H, 2×m), 7.89-7.71(4H, 2×d), 3.59-3.01 (8H, m), 2.03-1.84(6H, m)

EXAMPLE 4

6-(4-Aminopiperidin-1-yl)-9-(4-chlorophenyl)-9H-purine-2-carbonitrile, trifluoroacetate salt MS: APCI(+ve) 354(M+1) 1H NMR: (DMSO-d6) δ 8.86-8.84(1H, s), 7.98-7.71(6H, 2×d+m), 3.49-3.30(5H, m), 2.12-1.50(4H, m)

EXAMPLE 5

6-[(2-Aminoethyl)amino]-9-(4-chlorophenyl)-9H-purine-2-carbonitrile, acetate salt MS: APCI(+ve) 314(M+1) 1H NMR: (DMSO-d6) δ 8.82(1 H, s), 8.59(1 H, m), 7.89-7.70(4H, 2×d), 3.94(2H, brm), 3.55-3.51(2H, t), 2.83-2.80(2H, t), 1.88(3H, s)

EXAMPLE 6

9-(4-Chlorophenyl)-6-(dimethylamino)-9H-purine-2-carbonitrile

MS: APCI(+ve) 299(M+1) 1H NMR: (DMSO-d6) δ 8.80-8.79(1H, s), 7.88-7.69(4H, 2×d), 3.77(3H, m), 3.12(3H, m)

EXAMPLE 7

9-(4-Methylphenyl)-6pyrrolidin-1-yl-9H-purine-2-carbonitrile

MS: APCI(+ve) 305(M+1) 1H NMR: (DMSO-d6) δ 8.71 (1H, s), 7.68-7.42(4H, 2×d), 4.15-4.12(2H, t), 3.69-3.65(2H, t), 2.40(3H, s), 2.08-1.93(4H, m)

EXAMPLE 8

9-(4-Methoxyphenyl)-6pyrrolidin-1-yl-9H-purine-2-carbonitrile

MS: APCI(+ve) 321(M+1) 1H NMR: (DMSO-d6) δ 8.66 (1H, s), 7.69-7.15(4H, 2×d), 4.15-4.12(2H, t), 3.84(3H, s), 3.68-3.65(2H, t), 2.06-1.93(4H, m)

EXAMPLE 9

9-(4-chlorophenyl)-6-pyrrolidin-1-yl-9H-purine-2-carbonitrile

MS: APCI(+ve) 325(M+1) 1H NMR: (DMSO-d6) δ 8.08 (1H, s), 7.65(2H, d), 7.54(2H, d), 4.21(2H, t), 3.79(2H, t), 2.16-2.09(2H, m), 2.05-1.99(2H, m)

EXAMPLE 10

9-(4Chlorophenyl)-6-(ethylamino)-9H-purine-2-carbonitrile

MS: APCI(−ve) 297(M−1) 1H NMR: (DMSO-d6) δ 8.80 (1H, s), 8.63(1H, t), 7.88(2H, d), 7.72(2H, d), 3.57-3.50(2H, m), 1.21(3H, t)

EXAMPLE 11 tert-Butyl 4-[9-(4-chlorophenyl)-2-cyano-9H-purin-6yl]piperazine-1-carboxylate

MS: APCI(+ve) 440(M+1) 1H NMR: (CDCl3) δ 8.10(1H, s), 7.63(2H, d), 7.55(2H, d), 4.50-4.40(4H, brs), 3.62-3.59 (4H, m), 1.51(9H, s)

EXAMPLE 12

9-(4Chlorophenyl)-6piperazin-1-yl-9H-purine-2-carbonitrile

A solution of the product from example 11 (0.27 g) in dichloromethane (10 ml) and trifluoroacetic acid (5 ml) was stirred at room temperature for 0.5 h then evaporated under reduced pressure. The residue was purified by chromatography on silica eluting with 0.4% triethylamine/6% methanol in dichloromethane. Yield 0.06 g MS: APCI(+ve) 340(M+1) 1H NMR: (CDCl3) δ 8.08(1H, s), 7.63(2H, d), 7.54(2H, d), 4.60-4.00(4H, brs), 3.03(4H, t)

EXAMPLE 13

9-(2-Chlorophenyl)-4-morpholin-4-yl-9H-purine-2-carbonitrile

(i) 4-[6-Chloro-5-nitro-2-(propylthio)pyrimidin4-yl]morpholine

Morpholine (2.6 g) was added dropwise to a stirred solution of 4,6-dichloro-5-nitro-2-propylthiopyrimidine (8 g) and N,N-diisopropylethylamine (3.85 g) in acetonitrile (70 ml) at 0° C. After 1 h the solvent was evaporated and the residue partitioned between ethyl acetate and water, the organics dried (MgSO4) and evaporated under reduced pressure. The residue was purified by chromatography on silica eluting with 25% ethyl acetate in isohexane. Yield 7.1 g MS: APCI(+ve) 319(M+1)

(ii) N-(2-Chlorophenyl)-6-morpholin-4-yl-5-nitro-2-(propylthio)pyrimidin4-amine A mixture of the product from step (i) (1 g), 2-chloroaniline (0.4 g) and N,N-diisopropylethylamine (0.404 g) in isopropylalcohol (12ml) was heated at 55° C. for 14 h. The mixture was cooled and the isopropylalcohol decanted off. Yield 0.82 g MS: APCI(+ve) 410(M+1)

(iii) N~4~-(2-Chlorophenyl)-6-morpholin-4-yl-2-(propylthio)pyrimidine-4,5-diamine A mixture of the product from step (ii) (0.82 g) and iron powder (1.2 g) in glacial acetic acid (40 ml) was stirred at room temperature until the starting material was consumed. The solvent was removed under reduced pressure and the residue partitioned between ethyl acetate and aqueous sodium hydrogen carbonate solution. The organics were dried (MgSO4) and evaporated under reduced pressure. Crude yield 0.82 g MS: APCI(+ve) 380/2(M+1)

(iv) 9-(2-Chlorophenyl)-6morpholin-4-yl-2-(propylthio)-9H-purine

A solution of the product from step (i) (0.82 g) in diethoxymethylacetate (8 ml) was heated at 80° C. for 16 h. The mixture was added dropwise to a vigorously stirred mixture of water and isohexane (300 ml, 1:1), ethyl acetate added, the organic layer dried (MgSO4) and evaporated under reduced pressure. The residue was purified by chromatography on silica eluting with 25% ethyl acetate in isohexane. Yield 0.42 g MS: APCI(+ve) 390/2(M+1)

(v) 9-(2-Chlorophenyl)-6-morpholin-4-yl-2-(propylsulfonyl)-9H-purine

A mixture of the product from step (iv) (2.8 g) and 3-chloroperoxybenzoic acid (0.63 g, Aldrich 77% max.) in dichloromethane (15 ml) was stirred at room temperature for 5 h, washed with aqueous sodium metabisulphite solution, water, aqueous sodium hydrogencarbonate solution, water, dried (MgSO4) and evaporated under reduced pressure. Crude yield 0.74 g MS: APCI(+ve) 422/4 (M+1)

(vi) 9-(2-Chlorophenyl)-6-morpholin-4-yl-9H-purine-2-carbonitrile

Sodium cyanide (0.086 g) was added to a solution of the product from step (v) (0.74 g) in dimethylsulphoxide (10 ml) and heated at 60° C. for 36 h. The mixture was partitioned between ethyl acetate and brine, the organics washed with brine, dried (MgSO4) and evaporated under reduced pressure. The residue was purified by chromatography on silica eluting with 16% ethyl acetate in toluene. Yield 0.152 g MS: APCI(+ve) 341(M+1) 1H NMR: (DMSO-d6) δ 8.69 (1H, s), 7.80(1H, d), 7.73-7.60(3H, m), 3.78(4H, t).

EXAMPLES 14-18

Examples 14-18 were prepared according to the general method of example 13 using the appropriate amines.

EXAMPLE 14

9-(3,4-Difluorophenyl)-6-morpholin-4-yl-9H-purine-2-carbonitrile

MS: APCI(+ve) 343(M+1) 1H NMR: (DMSO-d6) δ 8.83 (1H, s), 8.06-8.01(1H, m), 7.79-7.71(2H, m), 3.77(4H, t)

EXAMPLE 15

9-(4-Isopropylphenyl)-6-morphilin-4-yl-9H-purine-2-carbonitrile

MS: APCI(+ve) 349(M+1) 1H NMR: (DMSO-d6) δ 8.77 (1H, s), 7.68(2H, d), 7.50(2H, d), 3.76(4H, t), 3.04-2.97(1H, m), 1.26(6H, d)

EXAMPLE 16

9-(4-Methoxyphenyl)-6-morpholin-4-yl-9H-purine-2-carbonitrile

MS: APCI(+ve) 337(M+1) 1H NMR: (DMSO-d6) δ 8.73 (1H, s), 7.67(2H, d), 7.16(2H, d), 4.20(4H, broad S), 3.85(3H, s), 3.76(4H, t)

EXAMPLE 17

9-(3-Chlorophenyl)-6-morpholin-4-yl-9H-purine-2-carbonitrile

MS: APCI(+ve) 341(M+1) 1H NMR: (DMSO-d6) δ 8.87 (1H, s), 7.98(1H, s), 7.85-7.82(1H, m), 7.68(1H, t), 7.62-7.59 (1H, m), 4.25(4H, broad S), 3.77(4H, t)

EXAMPLE 18

9-[4-(Methylsulfonyl)phenyl]-6morpholin-4-yl-9H-purine-2-carbonitrile

MS: APCI(+ve) 385(M+1) 1H NMR: (DMSO-d6) δ 8.95(1 H, s), 8.20(2H, d), 8.13(2H, d), 4.80-3.90(4H, brs), 3.77(4H, t)

EXAMPLE 19

6-[(4-Chlorophenyl)amino]-9-ethyl-9H-purine-2-carbonitrile

(i) 2-Chloro-N-(4-chlorophenyl)-9H-purin-6-amine

A mixture of 4-chloroaniline (1.35 g) and 2,6-dichloropurine (1 g) in n-butanol (15 ml) was heated at 100° C. for 3 h. The precipitate was filtered off, partitioned between ethyl acetate and aqueous sodium hydroxide solution, the organics dried (MgSO4), and evaporated under reduced pressure. The residue was triturated with ethyl acetate and filtered. Yield 1.04 g MS: APCI(+ve) 280/2(M+1)

(ii) 2-Chloro-N-(4-chlorophenyl)-9-ethyl-9H-purin-6-amine

A mixture of the product from step (i) (1.04 g), potassium carbonate (1.025 g) and ethyl iodide (0.637 g) in N,N-dimethylformamide (15 ml) was stirred vigorously at room temperature for 2 h. The mixture was partitioned between ethyl acetate and water, the organics washed with water, dried (MgSO4) and evaporated under reduced pressure. The residue was purified by chromatography on silica eluting with 2:1 ethyl acetate in isohexane. Yield 0.63 g MS: APCI(+ve) 308/310(M+1)

(iii) N-(4-Chlorophenyl)-9-ethyl-2-(methylthio)-9H-purin-6-amine

A mixture of the product from step (ii) (0.6 g) and sodium thiomethoxide (0.45 g) in dimethylsulphoxide (15 ml) was heated at 110° C. for 4 h. The mixture was partitioned between ethyl acetate and water, the organics washed with water, dried (MgSO4) and evaporated under reduced pressure. Yield 0.45 g MS: APCI(+ve) 320/322(M+1)

(iv) N-(4-Chlorophenyl)-9-ethyl-2-(methylsulfonyl)-9H-purin-6-amine

A mixture of the product from step (iii) (0.45 g) and 3-chloroperoxybenzoic acid (1.2 g, Aldrich 77% max.) in ethanol (20 ml) was stirred at room temperature for 4 h, ethyl acetate was added, the mixture washed with aqueous sodium metabisulphite solution, water, aqueous sodium hydrogencarbonate solution, water, dried (MgSO4) and evaporated under reduced pressure. The residue was purified by chromatography on silica eluting with 4:1 ethyl acetate in isohexane. Yield 0.39 g MS: APCI(+ve) 352/4 (M+1)

(v) 6-[(4-Chlorophenyl)amino]-9-ethyl-9H-purine-2-carbonitrile

A mixture of the product from step (iv) (0.13 g) and sodium cyanide (0.054 g) in dimethylsulphoxide (3 ml) was stirred at room temperature for 72 h then partitioned between ethyl acetate and water. The organic layer was washed with water, dried (MgSO4), evaporated under reduced pressure and the residue purified by chromatography on silica eluting with 2:1 ethyl acetate in isohexane. Yield 0.035 g MS: APCI(−ve) 297(M−1) 1H NMR: (DMSO-d6) δ 10.54 (1H, s), 8.62(1H, s), 7.90(2H, d), 7.44(2H, d), 4.28(2H, q), 1.46(3H, t)

EXAMPLE 20

9-(4-Chlorophenyl)-6-morpholin-4-yl-9H-purine-2-carbonitrile

(i) N-(4-Chlorophenyl)-6-morpholin-4-yl-5-nitro-2-(propylthio)pyrimidin-4-amine Morpholine (1.31 ml) was added dropwise to a stirred solution of 4,6-dichloro-5-nitro-2-thiopropyl pyrimidine (4 g) and N,N-diisopropylethylamine (7 ml) in dichloromethane (50 ml) at 0° C. After 1 h, 4-chloroaniline (1.9 g) was added, the mixture stirred at room temperature for 24 h, then heated under reflux for 24 h. The mixture was partitioned between dichloromethane and 2M hydrochloric acid, the organics washed with water, dried (MgSO4) and evaporated under reduced pressure. Yield 5 g MS: APCI(+ve) 410/2 (M+1)

(ii) 4-[(4-Chlorophenyl)amino]-6-morpholin-4-yl-5-nitropyrimidine-2-carbonitrile A mixture of the product from step (i) (5 g) and 3-chloroperoxybenzoic acid (12 g, Aldrich 77% max.) in dichloromethane (200 ml) was stirred at room temperature for 2 h, washed with aqueous sodium metabisulphite solution, water, aqueous sodium hydrogencarbonate solution, water, dried (MgSO4) and evaporated under reduced pressure. The solid was dissolved in dimethylsulphoxide (30 ml), sodium cyanide (2 g) added and stirred for 1 h at room temperature. Water (500 ml) was added and the solid filtered, washed with water, dried and the residue triturated with ether. Yield 1.7 g MS: APCI(+ve) 361/3 (M+1)

(iii) 5-Amino4-1(4-chlorophenyl)aminol-6-morpholin-4-ylpyrimidine-2-carbonitrile The product from step (ii) (1.7 g) and 10% palladium on charcoal (0.2 g) in ethyl acetate (300 ml) was hydrogenated at 2 Bar for 8 h, filtered through celite and the solvent evaporated under reduced pressure. Yield 1.05 g MS: APCI(+ve) 329/331 (M+1)

(iv) 9-(4-Chlorophenyl)-6-morpholin-4-yl-9H-purine-2-carbonitrile

A solution of the product from step (iii) (0.35 g) in diethoxymethylacetate (10 ml) was heated at 80° C. for 12 h, water added and the precipitate filtered. The solid was purified by chromatography on silica eluting with 30-40% ethyl acetate in isohexane. Yield 0.26 g MS: ESI 341 (M+1) 1H NMR: (DMSO-d6) δ 8.84(1H, s), 7.86(2H, d), 7.72(2H, d), 3.78-3.75(4H, m), 4.3(4H, brs)

EXAMPLE 21

8-Amino-6-[(4-chlorophenyl)amino]-9-ethyl-9H-purine-2-carbonitrile

A solution of 5-amino-4-[(4-chlorophenyl)amino]-6-(ethylamino)pyrimidine-2-carbonitrile (0.41 g, prepared using the method of example 20) in acetonitrile (5 ml) was added to a stirred solution of FMOC-NCS (0.44 g) in acetonitrile (10 ml) at 0° C. After 1 h, diisopropylcarbodiimide (0.252 g) was added, the mixture heated under reflux for 4 h, cooled, piperazine (0.1 g) added and stirred at room temperature for 3 h. The solvent was removed under reduced pressure and the residue partitioned between ethyl acetate and brine, the organics dried (MgSO4) and evaporated under reduced pressure. The solid was purified by chromatography on silica eluting with 2-4% methanol in dichloromethane. Yield 0.12 g MS: APCI(+ve) 314(M+1) 1H NMR: (DMSO-d6) δ 9.62 (1H, s), 7.83(2H, d), 7.37(2H, d), 7.14(2H, s), 4.08(2H, q), 1.26(3H, t)

EXAMPLE 22

8-Amino-9-(4-chlorophenyl)-6-morpholin-4-yl-9H-purine-2-carbonitrile

A mixture of the product from example 20 step (iii) (0.6 g) and FMOC-NCS (0.613 g) in dichloromethane was heated at 40° C. for 10 h. The mixture was cooled, 1,4-diisopropylcarbodiimide (0.422 ml) was added, heated for 5 h then piperidine (1 ml) added and stirred at room temperature for 3 h. The solvent was evaporated under reduced pressure, the residue triturated with ether and recrystallised form water and dimethylsulphoxide. Yield 0.344 g MS: APCI(+ve) 356/8(M+1) 1H NMR: (DMSO-d6) δ 7.68 (2H, d), 7.52(2H, d), 6.97(2H, s), 4.15-4.08(4H, m), 3.73-3.71(4H, m)

EXAMPLE 23

9-(4-Chlorophenyl)-6morpholin-4-yl-8-oxo-8,9-dihydro-7H-purine-2-carbonitrile Triphosgene (0.09 g) was added to a mixture of the product from example 20 step (iii) (0.4 g) and pyridine (0.4 ml) in dichloromethane (30 ml) and the mixture stirred at room temperature. After 1 h more triphosgene (0.02 g) was added, stirred for a further 1 h, water added and the solid filtered. The solid was washed with water, diethylether and dried. Yield 0.14 g MS: APCI(−ve) 355/7(M−1) 1H NMR: (DMSO-d6) δ 11.90(1H, s), 7.66-7.61(4H, m), 3.73-3.71(4H, m), 3.62-3.59 (4H, m)

EXAMPLE 24

9-(4-Chlorophenyl)-8-(dimethylamino)-6morpholin-4-yl-9H-purine-2-carbonitrile A mixture of the product from example 20 step (iii) (0.2 g) and dimethylthiocarbamoyl chloride (0.1 g) in acetonitrile (15 ml) was heated at 60° C. for 6 h. The precipitate was filtered, the filtrate evaporated under reduced pressure and the residue purified by chromatography on silica eluting with 40% ethyl acetate in isohexane. Yield 0.034 g MS: APCI(+ve) 384(M+1) 1H NMR: (DMSO-d6) δ 7.68 (2H, d), 7.58(2H, d), 4.15(4H, brs), 3.75-3.72(4H, m), 2.76 (6H, s)

EXAMPLE 25

7-(4-Chlorophenyl)-4-morpholin-4-yl-7H-pyrrolo[2,3-d]pryimidine-2-carbonitrile

(i) 5-Allyl-2,6-dichloro-N-(4-chlorophenyl)pyrimidin-4-amine

A mixture of 5-allyl-2,4,6-trichloropyrimidine (7 g), 4-chloroaniline (4 g) and potassium carbonate (4.27 g) in ethanol (100 ml) was stirred at room temperature for 24 h. The mixture was partitioned between ethyl acetate and water, the organics dried (MgSO4), and evaporated under reduced pressure. The residue was purified by chromatography on silica eluting with isohexane/diethylether (2:1). Yield 5 g MS: APCI(+ve) 314 (M+1)

(ii) {2,4-Dichloro-6-[(4-chlorophenyl)amino]pyrimidin-5yl}acetaldehyde

A solution of the product from step (i) (2 g) in dichloromethane (40 ml) was added to a solution of osmium tetroxide (1 ml, 2.5% wt in isopropylalcohol) and 4-methylmorpholine N-oxide (1.12 g) in dichloromethane (1 ml). After stirring at room temperature for 24 h the mixture was washed with water, aqueous sodium sulphite solution, dried (MgSO4) and evaporated under reduced pressure. The residue was dissolved in methanol (40 ml), cooled to 0° C. and lead tetraacetate (3.85 g) added. After 1 h the mixture was diluted with water, extracted with ethyl acetate, the organics dried (MgSO4) and evaporated under reduced pressure. Yield 2 g MS: APCI(+ve) 316 (M+1)

(iii) 2,4-Dichloro-7-(4-chlorophenyl)-7H-pyrrolo[2,3-d]pyrimidine

A solution of the product from step (ii) (2 g) and p-toluenesulfonic acid (catalytic) in methanol (30 ml) was stirred at room temperature for 2 h then evaporated under reduced pressure. The residue was purified by chromatography on silica eluting with isohexane/diethylether (2:1). Yield 0.5 g MS: APCI(+ve) 298/300 (M+1)

(iv) 7-(4-Chlorophenyl)-2,4-bis(ethylsulfonyl)-7H-pyrrolo[2,3-d]pyrimidine

Sodium ethanethiolate. (0.437 g) was added to a solution of the product from step (iii) (0.5 g) in dimethylsulphoxide (20 ml), stirred at room temperature for 30 min then partitioned between ethyl acetate and water. The organics were dried (MgSO4) and evaporated under reduced pressure. The residue was dissolved in dichloromethane (20 ml), 3-chloroperoxybenzoic acid (1.5 g, Aldrich 77% max.) added, the mixture stirred at room temperature for 2 h, washed with aqueous sodium metabisulphite solution, water, aqueous sodium hydrogencarbonate solution, water, dried (MgSO4) and evaporated under reduced pressure. Crude yield 1 g MS: APCI(+ve) 414 (M+1)

(v) 7-(4-Chlorophenyl)-4morpholin-4-yl-7H-pyrrolo[2,3-d]pryimidine-2-carbonitrile A mixture of the product from step (iv) (0.35 g), morpholine (0.11 ml) and N,N-diisopropylethylamine (0.22 ml) in tetrahydrofuran (10 ml) was stirred at room temperature for 24 h. The mixture was partitioned between ethyl acetate and water, the organics dried (MgSO4) and evaporated under reduced pressure. The residue was dissolved in N,N-dimethylformamide (10 ml), sodium cyanide (0.083 g) added and the mixture heated at 90° C. for 10 h. Water was added, the solid filtered off then purified by RPHPLC 25-95% acetonitrile in aqueous trifluoroacetic acid. Yield 0.075 g MS: APCI(+ve) 340 (M+1) 1H NMR: (DMSO-d6) δ 7.94-7.64(5H, m), 7.11(1H, m), 3.94-3.74(8H, m)

EXAMPLE 26

7-(4-Chlorophenyl)-4-(ethylamino)-7H-pyrrolo[2,3-d]pyrimidine-2-carbonitrile

The above named example was prepared according to the general method of example 25 using the appropriate amine.

MS: APCI(+ve) 298 (M+1) 1H NMR: (DMSO-d6) δ 8.26 (1H, t), 7.81-7.63(5H, m), 6.95-6.94(1H, m), 3.55-3.49(2H, q), 1.25-1.21(3H, t)

EXAMPLE 27

4-[(4-Chlorophenyl)amino]-7-ethyl-7H-pyrrolo[2,3-d]pyrimidine-2-carbonitrile (i) 4-Chloro-7-ethyl-2-(methylthio)-7H-pyrrolo[2,3-d]pyrimidine Sodium hydride (0.44 g, 60% dispersion in oil) was added portionwise to a stirred solution of 4-chloro-2-(methylthio)-7H-pyrrolo[2,3-d]pyrimidine (2 g) in N,N-dimethylformamide (30 ml) at 0° C. After 0.75 h, ethyl iodide (0.88 ml) was added, the mixture stirred for 2 h, quenched with water and partitioned between ethyl acetate and brine. The organics were washed with water, dried (MgSO4), evaporated under reduced pressure and the residue purified by chromatography on silica eluting with 15% ethyl acetate in isohexane. Yield 1.98 g MS: APCI(+ve) 228/230 (M+1)

(ii) N-(4-Chlorophenyl)-7-ethyl-2-(methylthio)-7H-pyrrolo[12,3-d]pyrimidin-4-amine A solution of the product from step (i) (0.5 g) and 4-chloroaniline (0.84 g) in ethanol (10 ml) was heated under reflux for 24 h then the solvent evaporated under reduced pressure. The residue was partitioned between ethyl acetate and 2M hydrochloric acid, the organics washed with water, dried (MgSO) and evaporated under reduced pressure. Yield 0.7 g MS: APCI(+ve) 319/321 (M+1)

(iii) N-(4-Chlorophenyl)-7-ethyl-2-(methylsulfonyl)-7H-pyrrolo[2,3-d]pyrimidin-4-amine A mixture of the product from step (ii) (0.7 g) and 3-chloroperoxybenzoic acid (1.38 g, Aldrich 77% max.) in dichloromethane (30 ml) was stirred at room temperature for 1 h, washed with aqueous sodium metabisulphite solution, water, aqueous sodium hydrogencarbonate solution, water, dried (MgSO4) and evaporated under reduced pressure. The residue was purified by chromatography on silica eluting with 50% ethyl acetate in isohexane. Yield 0.37 g MS: APCI(+ve) 351/3 (M+1)

(iv) 4-[(4-Chlorophenyl)amino]-7-ethyl-7H-pyrrolo[2,3-d]pyrimidine-2-carbonitrile Sodium cyanide (0.103 g) was added to a solution of the product from step (iii) (0.37 g) in dimethylsulphoxide (10 ml) and heated at 90° C. for 48 h. The mixture was partitioned between ethyl acetate and water, the organics dried (MgSO4) and evaporated under reduced pressure. The residue was purified by RPHPLC eluting with 29-95% acetonitrile in aqueous trifluoroacetic acid. Yield 0.14 g MS: APCI(+ve) 298/300(M+1) 1H NMR: (DMSO-d6) δ 9.94(1H, s), 7.83(2H, d), 7.67(1H, d), 7.46(2H, d), 6.93(1H, d), 4.26(2H, q), 1.38(3H, t) Mpt 183° C.

EXAMPLE 28

1-[7-(4-Chlorophenyl)-2-cyano-6,7-dihydro-5H-pyrrolo[2,3-d]pyrimidin-4-yl]-L-prolinamide (i) Methyl 2-oxotetrahydrofuran-3-carboxylate Cyclopropane-1,1-dicarboxylic acid (10 g) in acetonitrile (200 ml) was treated with triethylamine (43 ml) and iodomethane (19 ml) at room temperature. The solution was stirred for 2 h then heated at 75° C. for 16 h. The solvent was removed under reduced pressure, the residue dissolved in water, extracted with ethyl acetate, dried(MgSO4) and evaporated to a brown oil (6.70 g).

1H NMR: (CDCl3) δ 4.55-4.30(2H, m), 3.82(3H, s), 3.59-3.55(1H, m), 2.73-2.47(2H, m).

(ii) 5-(2-Hydroxyethyl)-2-thioxodihydropryimidine-4,6(1H,5H)-dione

A solution of the product from step (i) (6.70 g) in absolute ethanol (70 ml) was treated with thiourea (3.53 g) and triethylamine (12.80 ml). The mixture was heated at reflux for 16 h, the solvent was removed under reduced pressure and the solid dissolved in water (100 ml). The solution was acidified with conc. hydrochloric acid to pH2 and extracted with ethyl acetate. Continuous extraction of the aqueous layer with dichloromethane for 80 h gave a brown solid (2.20 g).

MS: APCI(+ve) 189(M+1)

(iii) 5-(2-Hydroxyethyl)-2-(methylthio)pryimidine-4,6(1H,5H)-dione

A solution of the product of step (ii) (2.2 g) in methanol(10 ml) was added to a solution of sodium (0.27 g) in methanol (90 ml). Iodomethane (0.73 ml) was added and the mixture heated at reflux for 1 hour. The solvent was removed under reduced pressure to give a solid.

MS: APCI(+ve) 203(M+1)

(iv) 4,6-Dichloro-5-(2-chloroethyl)-2-(methylthio)pyrimidine

The product from step (iii) and phosphorus oxychloride (30 ml) was heated at 100° C. for 3 h. The excess reagent was removed under reduced pressure, the residue quenched with ice-water, extracted with ethyl acetate, dried(MgSO4) and evaporated to an oil. The oil was purified by chromatography on silica eluting with isohexane:diethylether(4:1) to give a brown oil (0.36 g).

MS: APCI(+ve) 257/259(M+1)

(v) 4-Chloro-7-4-chlorophenyl)-2-(methylthio)-6,7-dihydro-5H-pyrrolo[2,3-d]pyrimidine A solution of the product from step (iv) (0.36 g) in acetonitrile (10 ml) was treated with 4-chloroaniline (0.18 g) and N,N-diisopropylethylamine (0.25 ml). The mixture was heated at 150° C., the solvent evaporated to form a melt which solidified after heating for 90 min. The solid was subjected to column chromatography eluting with isohexane:dichloromethane (1:1) to give a yellow solid (0.110 g).
MS: APCI(+ve) 312(M+1)

(vi) 4-Chloro-7-(4-chlorophenyl)-2-(methylsulfonyl)-6,7-dihydro-5H-pyrrolo[2,3-d]pyrimidine A mixture of the product from step (v) (0.11 g) and 3-chloroperoxybenzoic acid (0.15 g) in dichloromethane (20 ml) was stirred at room temperature for 2 h. The mixture was diluted with dichloromethane (100 ml) and washed with sodium metabisulphite solution followed by sodium hydrogencarbonate solution, dried(MgSO$_4$) and evaporated to an orange solid (0.1 g).
MS: APCI(+ve) 344(M+1)

(vii) 4-Chloro-7-4-chlorophenyl)-6,7-dihydro-5H-pyrrolo[2,3-d]pyrimidine-2-carbonitrile A mixture of the product from step (vi) (0.1 g) and sodium cyanide (0.022 g) in dimethylsulfoxide(10 ml) was stirred at room temperature for 2 h. The mixture was partitioned between ethyl acetate and water, the organics separated, dried (MgSO$_4$) and evaporated to a yellow solid (0.1 g).
MS: APCI(+ve) 291(M+1)

(viii) 1-[17-(4-Chlorophenyl)-2-cyano-6,7-dihydro-5H-pyrrolo[2,3-d]pyrimidin-4-yl]-L-prolinamide A mixture of the product from step (vii) (0.1 g), L-prolinamide (0.039 g) and N,N-diisopropylethylamine (0.09 ml) in dimethylsulphoxide(10 ml) was heated at 100° C. for 8 h. The mixture was partitioned between ethyl acetate and water, the organics separated, dried(MgSO$_4$) and evaporated under reduced pressure. The residue was purified by reverse phase HPLC using 50 to 95% acetonitrile in 0.1% ammonium acetate buffer to yield a white solid (0.03 g)
MS: APCI(+ve) 369(M+1) 1H NMR: (DMSO-d6) δ 7.72-7.02 (6H, m), 4.52-3.36 (7H, m), 2.14-1.90 (4H, m).

EXAMPLES 29-32

Examples 29-32 were prepared according to the method of example 28 steps(vi)-(viii).

EXAMPLE 29

1-[2-Cyano-7-(4-methoxyphenyl)-6,7-dihydro-5H-pyrrolo[2,3-d]pyrimidin-4-yl]-L-prolinamide MS: APCI(+ve) 365(M+1) 1H NMR: (DMSO-d6) δ 7.55-6.95 (6H, m), 4.51-3.67 (8H, m), 3.49-3.40 (2H, m), 2.13-1.89 (4H, m).

EXAMPLE 30

7-(4-Methoxyphenyl)-4-pyrrolidin-1-yl-6,7dihydro-5H-pyrrolo[2,3-d]pyrimidine-2-carbonitrile MS: APCI(+ve) 322(M+1) 1H NMR: (DMSO-d6) δ 7.55-6.94 (4H, m), 3.99-3.38 (11H, m), 1.89-1.85(4H, m).

EXAMPLE 31

7-(4-Methoxyphenyl)-4-morpholin-4-yl-6,7-dihydro-5H-pyrrolo[2,3-d]pyrimidine-2-carbonitrile MS: APCI(+ve) 338(M+1) 1H NMR: (DMSO-d6) δ 7.55-7.51 (2H, d), 6.99-6.96 (2H, d), 4.04-3.60 (13H, m), 3.33-3.28 (2H, m).

EXAMPLE 32

1-(4-Methylphenyl)-4-morpholin-4-yl-1H-pyrazolo[3,4-d]pyrimidine-6-carbonitrile

MS: APCI(+ve) 321(M+1) 1H NMR: (DMSO-d6) δ 8.71 (1H, s), 7.89-7.87 (2H, d), 7.42-7.39 (2H, d), 4.04-3.97 (4H, m), 3.80-3.77 (4H, m).2.39 (3H, s).

Measurement of Cathepsin S Activity.

QFRET Technology (Quenched Fluorescent Resonance Energy Transfer) was used to measure the inhibition by test compounds of Cathepsin S-mediated cleavage of the synthetic peptide Z-Val-Val-Arg-AMC. Compounds were screened at five concentrations in duplicate and the pIC$_{50}$ values reported.

Synthetic substrate, 20 μM [final]Z-Val-Val-Arg-AMC in phosphate buffer were added to a 96 well black Optiplate. The assay plates were pre-read for compound auto fluorescence on SpectraMax Gemini at 355 nM excitation and 460 nM emission. 250 pM [final]rHuman Cathepsin S in phosphate buffer was added and incubated for 2 h at room temperature on the SpectraMax Gemini, taking readings every 20 min at 355 nM excitation and 460 nM emission.

Activity Based template (5PTB-8) used the auto fluorescent corrected data to calculate the percentage inhibition for each compound concentration using the relevent plate controls. This data was used to construct inhibition curves and pIC$_{50}$ estimated by non-linear regression using a 4 parameter logistic model.

The invention claimed is:
1. A compound of formula (I):

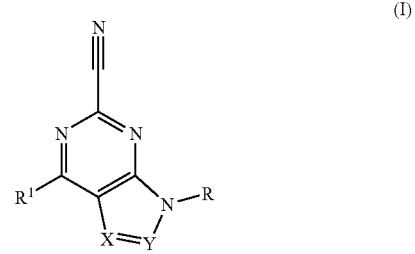

(I)

in which:
X is N;
Y is :CH, CO, CH$_2$ or :CNR$^2$R$^3$, where R$^2$ and R$^3$ are independently hydrogen, C$_{1-6}$ alkyl or C$_{3-6}$ cycloalkyl;
R is aryl or heteroaryl optionally substituted by halogen, amino, hydroxy, cyano, nitro, trifluoromethyl, carboxy, CONR$^5$R$^6$, SO$_2$NR$^5$R$^6$, SO$_2$R$^4$, NHSO$_2$R$^4$, NHCOR$^4$, ethylenedioxy, methylenedioxy, C$_{1-6}$ alkyl, C$_{1-6}$ alkoxy, SR$^4$ or NR$^5$R$^6$ where R4 is hydrogen, C$_{1-6}$ alkyl or C$_{3-6}$ cycloalkyl, R$^5$ and R$^6$ are independently hydrogen, C$_{1-6}$ alkyl or together with the nitrogen atom to which they are attached form a 5- or 6-membered saturated ring optionally containing a further O, S or NR$^4$ group;
or R is C$_{1-6}$ alkyl or C$_{3-6}$ cycloalkyl, R¹ is a group Y(CH₂)pR⁷ where p is 0, 1 or 2 and Y is O or NR⁸ where R⁸ is hydrogen, $C_{1-6}$ alkyl or $C_{3-6}$ cycloalkyl;

and R⁷ is a 5- or 6-membered saturated ring containing one or more O, S or N atoms, aryl or a heteroaryl group containing one to four heteroatoms selected from O, S or N, the saturated ring, aryl and heteroaryl groups all being optionally substituted by halogen, amino, hydroxy, cyano, nitro, trifluoromethyl, carboxy, CONR⁵R⁶, SO₂NR⁵R⁶, SO₂R⁴, NHSO₂R⁴, NHCOR⁴, $C_{1-6}$ alkyl, $C_{1-6}$ alkoxy, SR⁴ or NR⁵R⁶ where R4 is hydrogen, $C_{1-6}$ alkyl or $C_{3-6}$ cycloalkyl, R⁵ and R⁶ are independently hydrogen, $C_{1-6}$ alkyl or together with the nitrogen atom to which they are attached form a 5- or 6-membered saturated ring optionally containing a further O, S or NR⁴ group;

or R¹ is a group NR⁹R¹⁰ where R⁹ and R¹⁰ are independently hydrogen or $C_{1-6}$ alkyl, or R⁹ and R¹⁰ together with the nitrogen atom to which they are attached form a 5 or 6-membered saturated ring optionally containing a further O, S or N atom and optionally substituted by a second NR⁹R¹⁰ where R⁹ and R¹⁰ are independently hydrogen or $C_{1-6}$ alkyl or R⁹ and R¹⁰ together with the nitrogen atom to which they are attached form a 5- or 6-membered saturated ring optionally containing a further O, S or NR⁴, CO₂$C_{1-6}$ alkyl, CONR¹¹R¹² where R¹¹ and R¹² are independently hydrogen or $C_{1-6}$ alkyl, aryl or heteroaryl group optionally substituted by halogen, amino, hydroxy, cyano, nitro, trifluoromethyl, carboxy, CONR⁵R⁶, SO₂NR⁵R⁶, SO₂R⁴, NHSO₂R⁴, NHCOR⁴, $C_{1-6}$ alkyl, $C_{1-6}$ alkoxy, SR⁴ or NR⁵R⁶ where R4 is hydrogen, $C_{1-6}$ alkyl or $C_{3-6}$ cycloalkyl, R⁵ and R⁶ are independently hydrogen, $C_{1-6}$ alkyl or together with the nitrogen atom to which they are attached form a 5- or 6-membered saturated ring optionally containing a further O, S or NR⁴ group;

and pharmaceutically acceptable salts or solvates thereof.

2. A compound according to claim 1 in which X is N and Y is :CH.

3. A compound according to claim 1, wherein R is $C_{1-4}$alkyl, or phenyl substituted by halogen, SO₂Me, $C_{1-6}$alkoxy or $C_{1-4}$alkyl.

4. A compound according to claim 1, wherein R¹ is a group Y(CH₂)pR⁷ where p is 0 and Y is NR⁸ where R⁸ is hydrogen and R⁷ is substituted phenyl.

5. A compound according to claim 1, wherein R¹ is NR⁹R¹⁰ where R⁹ and R¹⁰ are hydrogen or $C_{1-3}$ alkyl or together with the nitrogen atom to which they are attached form a 5 or 6-membered saturated ring optionally containing a O, S or NR⁴.

6. A compound selected from:
1-[9-(4-Chlorophenyl)-2-cyano-9H-purin-6-yl]-L-prolinamide,
9-(4-Chlorophenyl)-6-(4-pyrrolidin-1-ylpiperidin-1-yl)-9H-purine-2-carbonitrile,
9-(4-Chlorophenyl)-6-[(3-pyrrolidin-1-ylpropyl)amino]-9H-purine-2-carbonitrile,
6-(4-Aminopiperidin-1-yl)-9-(4-chlorophenyl)-9H-purine-2-carbonitrile,
6-[(2-Aminoethyl)amino]-9-(4-chlorophenyl)-9H-purine-2-carbonitrile,
9-(4-Chlorophenyl)-6-(dimethylamino)-9H-purine-2-carbonitrile,
9-(4-Methylphenyl)-6-pyrrolidin-1-yl-9H-purine-2-carbonitrile,
9-(4-Methoxyphenyl)-6-pyrrolidin-1-yl-9H-purine-2-carbonitrile,
9-(4-chlorophenyl)-6-pyrrolidin-1-yl-9H-purine-2-carbonitrile,
9-(4-Chlorophenyl)-6-(ethylamino)-9H-purine-2-carbonitrile,
tert-Butyl 4-[9-(4-chlorophenyl)-2-cyano-9H-purin-6-yl]piperazine-1-carboxylate,
9-(4-Chlorophenyl)-6-piperazin-1-yl-9H-purine-2-carbonitrile,
9-(2-Chlorophenyl)-6-morpholin-4-yl-9H-purine-2-carbonitrile
9-(3,4-Difluorophenyl)-6-morpholin-4-yl-9H-purine-2-carbonitrile,
9-(4-Isopropylphenyl)-6-morpholin-4-yl-9H-purine-2-carbonitrile,
9-(4-Methoxyphenyl)-6-morpholin-4-yl-9H-purine-2-carbonitrile,
9-(3-Chlorophenyl)-6-morpholin-4-yl-9H-purine-2-carbonitrile,
9-[4-(Methylsulfonyl)phenyl]-6-morpholin-4-yl-9H-purine-2-carbonitrile,
6-[(4-Chlorophenyl)amino]-9-ethyl-9H-purine-2-carbonitrile,
9-(4-Chlorophenyl)-6-morpholin-4-yl-9H-purine-2-carbonitrile,
8-Amino-6-[(4-chlorophenyl)amino]-9-ethyl-9H-purine-2-carbonitrile,
8-Amino-9-(4-chlorophenyl)-6-morpholin-4-yl-9H-purine-2-carbonitrile,
9-(4-Chlorophenyl)-6-morpholin-4-yl-8-oxo-8,9-dihydro-7H-purine-2-carbonitrile,
9-(4-Chlorophenyl)-8-(dimethylamino)-6-morpholin-4-yl-9H-purine-2-carbonitrile,
and pharmaceutically acceptable salts thereof.

7. A pharmaceutical composition which comprises a compound of the formula (I) as defined in claim 1 or a pharmaceutically acceptable salt thereof and a pharmaceutically acceptable diluent or carrier.

8. A method for producing inhibition of at least one cysteine protease chosen from cathepsins S, K, L, F and B in a mammal comprising administering to said mammal an effective amount of a compound as defined in claim 1, or a pharmaceutically acceptable salt thereof.

9. A method for treating pain in a mammal in need of such treatment comprising administering to said mammal an effective amount of a compound as defined in claim 1, or a pharmaceutically acceptable salt thereof.

10. A method for inhibiting Cathepsin S in a warm blooded animal comprising administering a compound of the formula (I) as defined in claim 1 or a pharmaceutically acceptable salt thereof to a warm blooded animal.

11. A pharmaceutical composition which comprises a compound of the formula (I) as defined in claim 6 or a pharmaceutically acceptable salt thereof and a pharmaceutically acceptable diluent or carrier.

12. A method for producing inhibition of at least one cysteine protease chosen from cathepsins S, K, L, F and B in a mammal comprising administering to said mammal an effective amount of a compound as defined in claim 6, or a pharmaceutically acceptable salt thereof.

13. A method for treating pain in a mammal in need of such treatment comprising administering to said mammal an effective amount of a compound as defined in claim 6, or a pharmaceutically acceptable salt thereof.

14. A method for inhibiting Cathepsin S in a warm blooded animal comprising administering a compound of the formula (I) as defined in claim 6 or a pharmaceutically acceptable salt thereof to a warm blooded animal.

* * * * *